US005623096A

United States Patent [19]
Bandyopadhyay

[11] Patent Number: 5,623,096
[45] Date of Patent: Apr. 22, 1997

[54] ORTHOGONAL SHEAR STRESS MEASUREMENT PROBE ASSEMBLY FOR BOUNDARY LAYER FLOW

[75] Inventor: Promode R. Bandyopadhyay, Barrington, R.I.

[73] Assignee: The United States of America as represented by the Secretary of the Navy, Washington, D.C.

[21] Appl. No.: 491,693

[22] Filed: Jun. 19, 1995

[51] Int. Cl.⁶ .................................................. G01N 11/00
[52] U.S. Cl. .............................................................. 73/147
[58] Field of Search .............................. 73/866.5, 865.8, 73/774, 147

[56] References Cited

U.S. PATENT DOCUMENTS 3,382,712  5/1968  Lurry .......................................... 73/147
4,896,098  1/1990  Haritonidis et al. ..................... 324/663
5,052,228  10/1991  Haritonidis ................................ 73/147
5,199,298  4/1993  Ng et al. .................................... 73/147

*Primary Examiner*—Robert Raevis
*Attorney, Agent, or Firm*—Michael J. McGowan; Prithvi C. Lall; Michael F. Oglo

[57] ABSTRACT

An orthogonal shear stress measurement probe assembly is provided for measurements away from a solid surface or a vehicle wall. The assembly includes a plurality of micron-sized floating element drag sensors mounted on a 2 mm stainless steel needle. The needle is in turn supported by a streamlined probe which provides both a support for the needle-drag sensor assembly and a conduit for electrical lead. The electrical leads connect the drag sensing elements, which contain piezo-resistive elements, to an external portion of a bridge. These resistive elements form one-half of a bridge, the remaining bridge elements, amplifiers, read-out circuits and power supply are located outside the probe.

8 Claims, 4 Drawing Sheets

ORTHOGONAL SHEAR STRESS MEASUREMENT PROBE ASSEMBLY FOR BOUNDARY LAYER FLOW

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

(1) Technical Field of the Invention

The present invention relates generally to the field of measurement and testing instrumentation and in particular to sensors for the measurement of shear stresses in fluid flows.

(2) Description of the Prior Art

The transport of mass, momentum and concentration in a shear flow are governed by the stress sensor field. These flow characteristics produce direct and shearing stresses which owe their origin to viscosity. In potential flow theory, a fluid is "frictionless" with shear stress assumed to be zero, thereby allowing solutions to the flow equations as only direct stresses need to be considered. Potential flow solutions, while providing some general design information for airfoils or hydrofoils, are unsatisfactory for design problems involving high lift, laminar flow, stall, and other circumstances where boundary layer flow is important. Additionally, in a turbulent flow, the stress components have additionally the "Reynolds" or apparent stresses coming from the fluctuating velocities. These stress components are time dependent. For purposes of the invention herein, these apparent stresses are not considered.

Navier-Stokes equations are the fundamental equations of motions of a fluid. Using these equations, the shear stress components are not treated directly. They are derived in terms of rate of strain, that is, spatial velocity derivatives (see "Boundary-Layer Theory" by Schlichting 1979 7th ed. p. 58, McGraw-Hill, N.Y.). All measurements of shear stresses are made by measuring the instantaneous velocity field. These measurements must be carried out to a high degree of resolution as the derivatives are very Sensitive to such resolution. Using these methods, solution of the equations is dependent on the assumption that shear stresses are equal where the stress tensor elements differ only in the order of subscripts, that is, $\tau_{xy}=\tau_{yx}$. Using this assumption, the stress tensor matrix is symmetrical in relation to its principal diagonal. Without this assumption, the complexity of the flow and corresponding equations preclude solutions of the Navier-Stokes equations.

The development of devices which apply hydrostatic forces to a fluid, causing local movement proportional to the fluid volume, result in invalid results using the symmetric matrix assumptions. These devices include magneto-electrostatic drive systems which are currently under development for submarine or other undersea vehicle propulsion systems. In analytic development of such systems, it is necessary to measure shear stresses within and across the boundary layer. Shear stresses must be measured not only at a flow surface, but also throughout the thickness of the boundary layer.

Currently, the shear stresses are measured by three methods (or their variations): (1) hot-wire anemometry, (2) multiple component laser Doppler velocimetry (LDV) and (3) particle image velocimetry (PIV). The first method requires a precise calibration and only measure is shear stress indirectly. The latter two methods require no calibration and both measure the velocities directly. Once measurements are complete, the shear stress is then derived from the spatial derivatives of the measurements.

All these techniques have many drawbacks. Both the hot-wire or film anemometry are indirect methods. Both techniques are subject to temperature drift. Additionally, each is subject to physical and thermal interference caused by the probe. Further, the sensors are very fragile.

Further problems arise from the analytical assumptions involved in the derivation of the stresses from the measured voltage output. Also, the natural response of the sensor is nonlinear. Due to these reasons, the results can have uncertainties of 20% or even higher and the results are somewhat ambiguous. In the presence of an electric or magnetic field, the hot wire reliability may be affected due to induced current or voltage. Further, hot wire anemometry is also insensitive to flow direction.

The LDV technique also has many limitations. The probe volume is usually large. As a result, near wall measurements are difficult due to fringe interference, often requiring seeding of the flow. Without an adequate seeding, data can be lost and interpretation of the data Becomes ambiguous. Another unresolved problem of the technique is velocity bias. Further, alignment difficulties, vibration isolation, the difficulty of access through optical quality windows and the sheer bulk of the attendant laser and optics are also impediments. It is difficult, if not impossible to use it in a field test or in flight. When the flow field is unsteady, the burden of measurements in hot-wire and LDV which are point methods, increases greatly.

The PIV technique also has its drawbacks. Here, PIV includes the technique called holo-cinematography velocimetry (HCV). Currently, PIV is still under development. It is primarily being developed in low speed water flows where the Reynolds number is also low. It is extremely computer intensive. Unambiguous methods of tracking the particles are yet to be developed. The fluid must be seeded with appropriate neutrally buoyant spheres. This requirement precludes the use of the PIV technique in the ocean or in flight. It needs involved optics and photography. Furthermore, mobility of the technique is limited.

Alternatively, in laminar flows, the stress field can be simulated by Direct Numerical Simulation of the Navier-Stokes Equations. Although they are extremely well calibrated and verified over the years, two aspects of these equations should be noted which are in contrast to the present invention. First, the so called second stress factor of proportionality is obtained by Stokes's hypothesis and second, the stresses are indirectly derived from velocity derivatives.

SUMMARY OF THE INVENTION

It is an object of the invention to provide a drag sensor which can be used in operational environments including in-flight testing and in-ocean testing.

It is another object of the invention to provide a drag sensor for direct sensing of boundary layer shear forces.

It is yet another object of the invention to provide a drag sensor having improved accuracy.

It is a further object of the invention to provide a drag sensor having a direction sensing element.

It is yet a further object of the invention to provide a drag sensor having a dynamic response to local shear stress within a boundary layer.

Accordingly, the invention is a shear stress management probe comprising a plurality of rectangular floating elements mounted on a modified 2 mm needle which is in turn mounted on a streamlined probe. The rectangular floating elements have dimensions of approximately 100 µm (1 µm=$10^{-6}$ meters) by 150 µm by 5 µm mounted on flattened surfaces of the needle tip. Each element is supported by the sections of n-type silicone which act as tethers for the elements. When the element is acted on by a flow field, strain is developed within the tethers which is detected by piezo-resistors embedded within the tethers. The arrangement of elements on the tip and sides of the modified needle permit the detection of shear direction and magnitude for an orthogonal field. Detection of the stress components is accomplished by a wheatstone bridge arrangement wherein the piezo-resistors in the tethers form one-half of the bridge. The remaining bridge elements, amplifiers, read-out circuits and power supply are located outside the probe.

BRIEF DESCRIPTION OF THE DRAWINGS

The foregoing and other objects of the present invention will be more fully understood from the following detailed description and reference to the appended drawings wherein.

DESCRIPTION OF THE PREFERRED EMBODIMENTS

Figure 1:
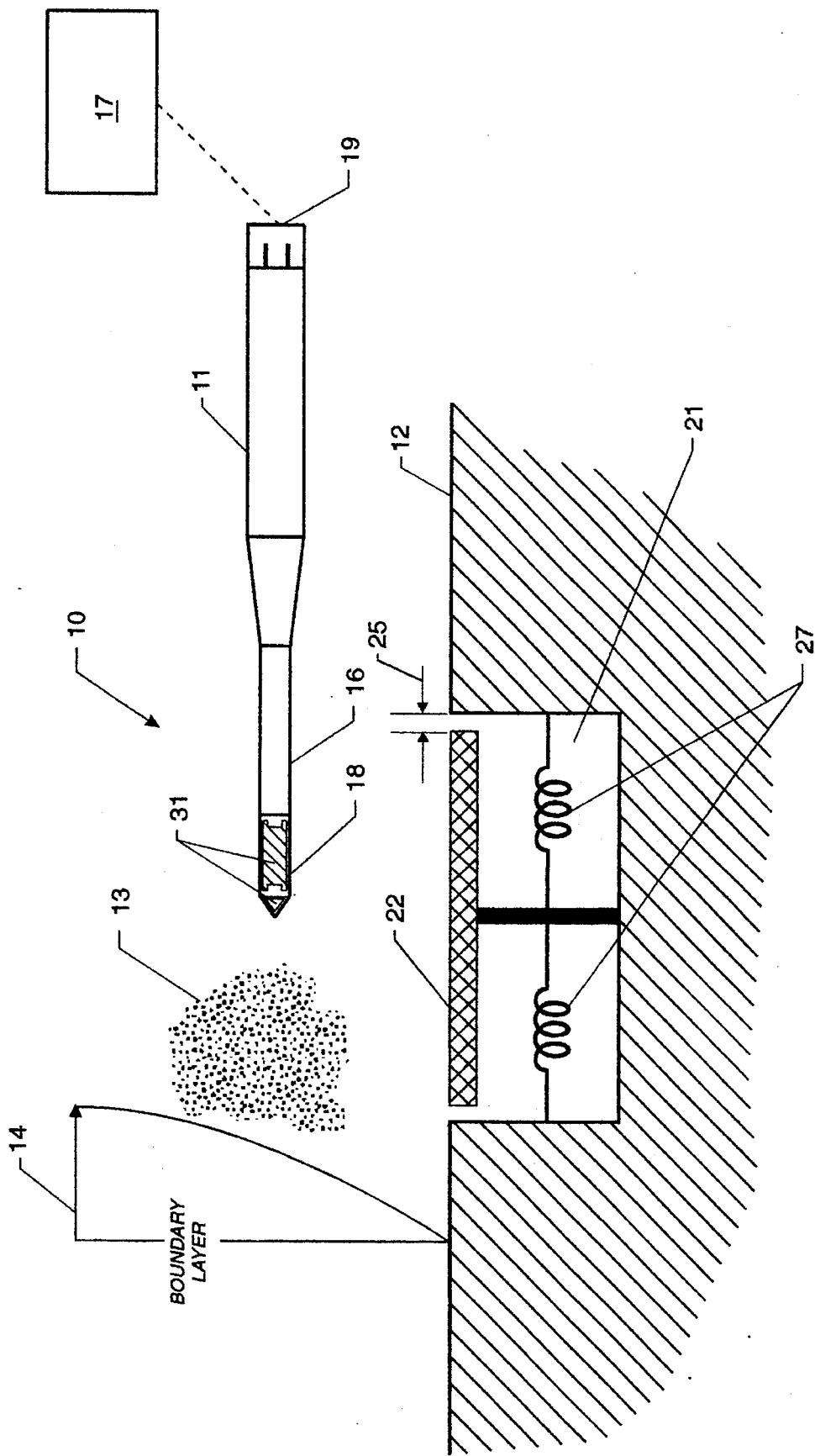
FIG. 1 is a side view of the orthogonal shear stress measurement probe mounted in a wind tunnel with a schematic view of a conventional prior art wall-mounted floating drag element mounted for comparison.

Referring now to FIG. 1, the orthogonal shear stress management streamlined probe is shown, designated generally by the reference numeral 10, as mounted in a wind tunnel (or water tunnel or a tow tank) above a conventional prior art wall-mounted floating element drag sensor 22. The typical prior art floating element drag sensor 22 is mounted in a cavity 21 embedded in the wall 12 of the wind tunnel. The relatively large size of the floating drag element generally precludes measurements away from the wall, i.e., in the middle of the boundary layer 14 velocity profile. The large size of the drag sensor in the prior art has been necessary due to the relatively small shear forces acting on the surface. Also shown in this figure are small gaps 25 at the leading and trailing edges of the drag element and the restoring mechanism 27 depicted here as nulling springs. The mechanical nature of the restoring force and the size of the element results in slow responses to unsteady flow fields. By comparison, the orthogonal shear stress management probe 10 is mounted away from the wall 12 positioned to sense boundary layer flow at any distance from the wall, depicted here as shear flow 13. The streamlined probe 11 has a capered leading edge with an inlet and a trailing edge with outlets for electrical leads. The streamlined probe 11 serves as a mount for a circular stainless steel needle 16, having a diameter of preferably two millimeters. The forward end of the needle is modified to make a square end providing a block 18 with flat sides having dimensions of approximately 200 µm×200 µm. The forward tip on the square end provides a sharp surface in the shape of a pyramid. The micron-sized floating element drag sensors 31 are attached to the flat sides of block 18 and to each of the four triangular faces of the pyramid-shaped tip. The electrical terminals 19 connect to the external portion of the bridge, amplifiers, readouts and power supply, depicted by block 17.

Figure 2:
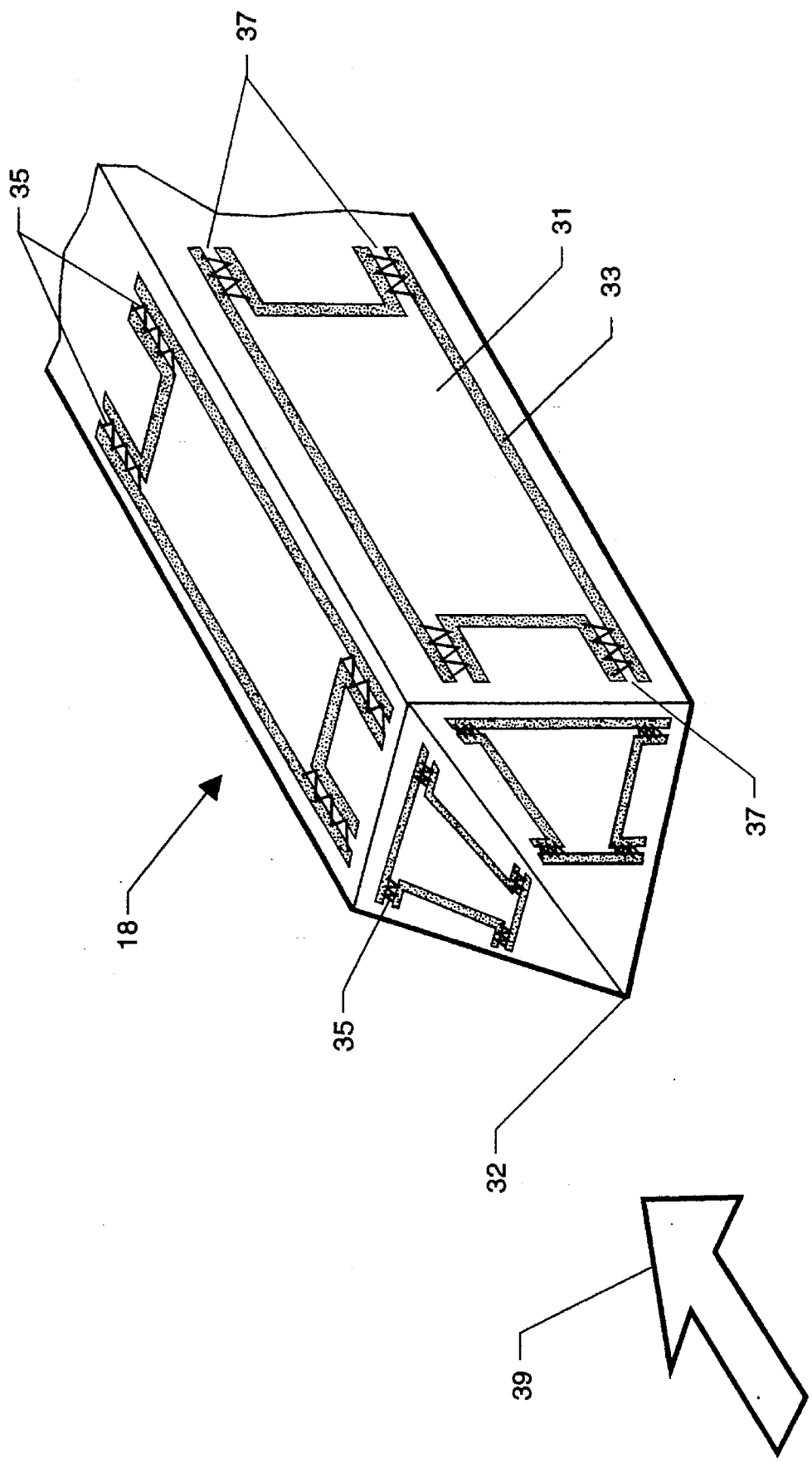
FIG. 2 is a perspective view of the modified needle portion in the preferred embodiment showing the placement of floating element drag sensors.

The physical configuration of the needle-drag element assembly is shown in FIG. 2. The floating elements 31 are connected at all four corners by tethers 37. Each tether contains piezo-resistive elements 35 (shown only in one tether for clarity) which provide electrical signals proportional to the stresses applied to the element. The entire floating element 31 is surrounded by a small gap 33 approximately 5 µm in width and is supported over a silicon substrate base. Each floating element is separated from the substrate base by an insulating layer (formed with silicon dioxide in the preferred embodiment) having a small cavity which in conjunction with the substrate base provides the operating cavity for the floating element. The element and tethers are fabricated using lightly-doped n-type silicon layers. The end portion of the 2 mm stainless steel needle is modified to form block 18 having a square pyramid tip 32. A plurality of micron-sized floating element drag elements 31 are attached to each side of the block 18 and to each side of the pyramid tip 32. Piezo-resistive elements located on the forces of the tip pyramid are oriented to provide shear stress measurements in the vertical and lateral planes relative to the longitudinal axis of the probe. By this orientation, shear stresses perpendicular to the main flow direction 39 are determined. Piezo-resistive elements located on the sides of block 18 detect shear stress along the longitudinal axis. By comparison of signals from opposite elements, that is, comparison of signals from the top and bottom or from the side to side, the angle-of-attack and the yaw angle can be determined relative to the local flow. The measurement of the orthogonal shear stresses at various points across the boundary provides values for correction of the stress tensor matrix used in standard viscous flow calculations. Once corrected, the stress tensor matrix can be used in the conventional manner to analytically evaluate design changes.

Figure 3:
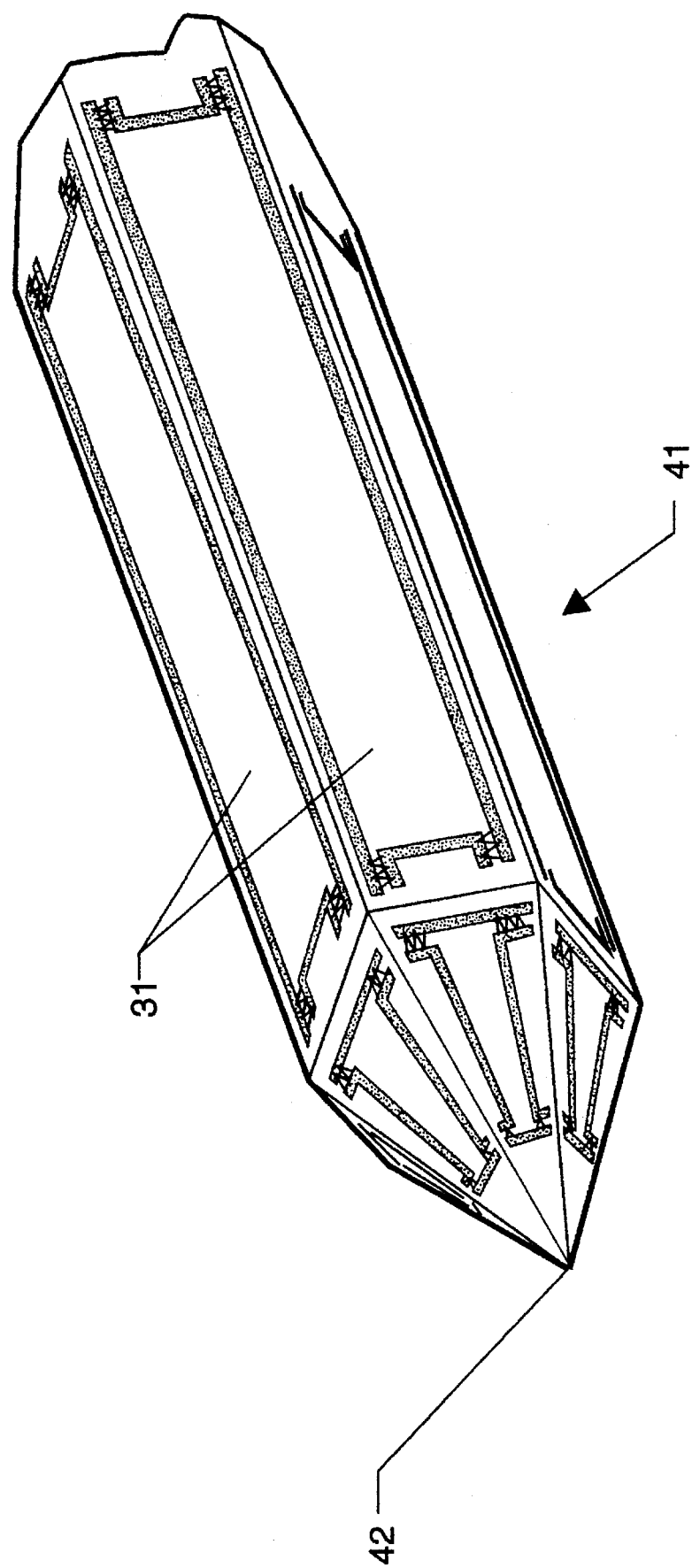
FIG. 3 is an alternative embodiment using a hexagonal arrangement of sensors.

Referring now to FIG. 3, an alternative embodiment of the invention is shown offering slightly improved resolution, but requiring more complex fabrication. In this embodiment, the stainless steel needle has been modified to a hexagon-shaped end forming a six-sided block 41 and the probe tip 42 has been modified forming a pyramid-shaped tip having six faces. Sensors on the pyramid faces are perpendicular to the flow in the same manner as in the previously described preferred embodiment. Sensors 31 along the sides of the block 41 are aligned with the longitudinal axis of the probe (in the direction of the main fluid flow).

OPERATION OF THE INVENTION

Figure 4:
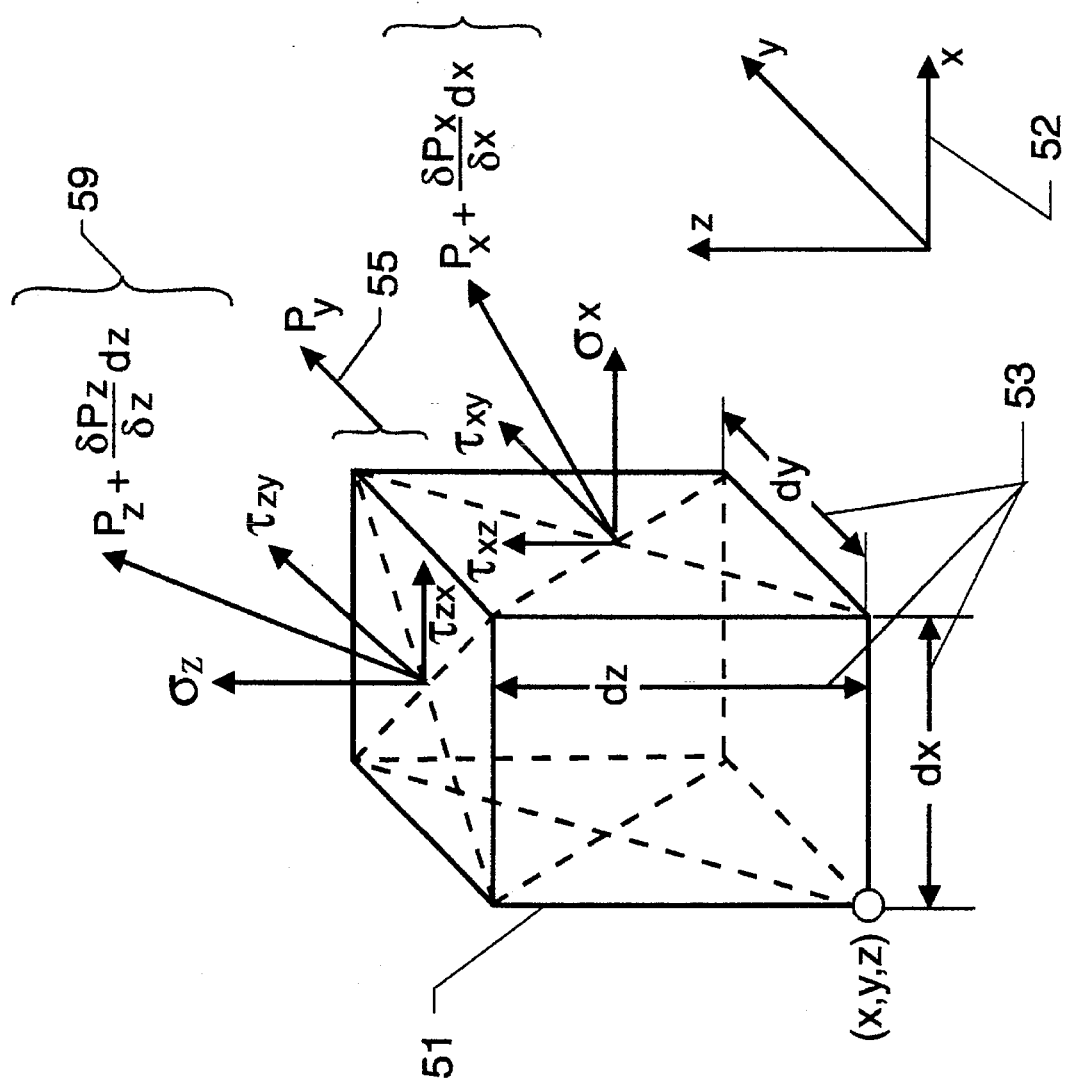
FIG. 4 is a schematic Of a small fluid volume showing the mathematical representation of shear stresses in the fluid.

Referring now to FIG. 4, a small parallepiped 51 of volume dV=dxdydz 53 is shown representing an isolated instantaneous portion of the fluid flow. On the faces of the parallepiped having area dy*dz, (perpendicular to the x-axis of the coordinate system 52), two resultant stress vectors 57 act $$PP_x \text{ and } P_x + \frac{\delta P_x}{\delta x} dx \qquad (1)$$

For each face the net components of surface forces 55, 57 and 59 perpendicular to each axis are $$x: \frac{\delta P_x}{\delta x} * dx * dy * dz \quad (2)$$

$$y: \frac{\delta P_y}{\delta y} * dx * dy * dz \quad (3)$$

$$z: \frac{\delta P_z}{\delta z} * dx * dy * dz. \quad (4)$$

and the resultant surface force P per unit volume is, therefore, given by $$P = \frac{\delta P_x}{\delta x} + \frac{\delta P_y}{\delta y} + \frac{\delta P_z}{\delta z}. \quad (5)$$

The vector quantities $P_x$, $P_y$ and $P_z$ can be resolved into components perpendicular to each face, labeled as $\sigma$ and components parallel to each face, the shearing stresses labeled as $\tau$ thereby providing $$P_x = i\sigma_x + j\tau_{xy} + k\tau_{xz} \quad (6)$$

$$P_y = i\tau_{yx} + j\sigma_y + k\tau_{yz} \quad (7)$$

$$P_z = i\tau_{zx} + j\tau_{zy} + k\tau_z \quad (8)$$

Solution of the resulting stress tensor $$\pi = \begin{bmatrix} \sigma_x & \tau_{xy} & \tau_{xz} \\ \tau_{yx} & \sigma_y & \tau_{yz} \\ \tau_{zx} & \tau_{zy} & \sigma_z \end{bmatrix} \quad (9)$$

is dependent on the simplifying assumption that the stress tensor and corresponding matrix are symmetrical, that is stress is equal for shearing stresses differing only in the order of the subscripts, i.e., $\tau_{xy} = \tau_{yx}$; $\tau_{xz} = \tau_{zx}$; $\tau_{yz} = \tau_{zy}$. In the event that hydrostatic forces are applied to the fluid (causing a local moment proportional to the volume), the stress tensor is no longer symmetric about its principal axis, that is $\tau_{xy} \neq \tau_{yx}$, $\tau_{xz} \neq \tau_{zx}$, and $\tau_{yz} \neq \tau_{zy}$. The use of electrostatic fields, to provide a propelling force to the fluid as used in electrostatic magnetic drive mechanisms, requires a means of measuring the values of the stress components. This measurement allows a correction for the non-symmetry of the stress tensor.

The features and advantages of the invention are numerous. Flow measurements can be made with little disruption of the flow field. The direction and amplitude of the actual values can be measured with a response sufficient to determine actual local flow (compared to mean value is previously achieved). The measurements can be made away from the wall of the flow body thereby measuring local stress across the boundary layer thickness. It is a fundamental aspect that the present invention stands apart in the sense that it measures the shear stress away from the wall and further that it measures stress directly and not through spatial velocity derivatives.

It will be understood that many additional changes in the details, materials, steps and arrangement of parts, which have been herein described and illustrated in order to explain the nature of the invention, may be made by those skilled in the art within the principle and scope of the invention as expressed in the appended claims. For example, a multiple-faced sensor can be fabricated having three or Six faces to simultaneously measure all stress forces. Additionally, the tethers may be arranged to provide non-parallel tethers or any given floating element can be replaced by a set of two or four adjacent elements to double or quadruple the sensitivity for improved dynamic response.

What is claimed is:

1. An orthogonal shear stress measuring probe assembly for measuring local flow within la boundary layer comprising:

a probe having a tapered leading edge with an inlet and a trailing end with outlets for electrical leads;

a needle having a circular end attached to the tapered end of said probe and a square end forming a block with flat sides, said square end having a pyramid-shaped tip having four triangular faces;

a plurality of micron-sized floating element drag sensors, said drag sensors being mounted on each of the sides of the block and on each of the faces of the pyramid-shaped tip;

electrical leads connected to said floating element drag sensors and leading through said needle and through said probe; and an external bridge including a power supply and instrument readouts.

2. An orthogonal shear stress measuring probe assembly as in claim 1 wherein said needle further comprises a needle fabricated from stainless steel.

3. An orthogonal shear stress measuring probe assembly as in claim 1 wherein each of said plurality of micron-sized floating element drag sensors comprises:

a silicon substrate base;

an insulating layer applied to said silicon substrate base having an open area in its center thereby forming a cavity with the silicon substrate base as the floor of the cavity;

an upper layer applied to said insulating layer, said upper layer having gaps cut to form a floating drag element having corners tethered to the remaining upper layer; and piezo-resistive elements imbedded in the tethers of said upper layer.

4. An orthogonal shear stress measuring probe assembly as in claim 3 wherein said insulating layer is fabricated with silicon dioxide.

5. An orthogonal shear stress measuring probe assembly as in claim 3 wherein said upper layer is a lightly-dope n-type silicon.

6. An orthogonal shear stress measuring probe assembly for measuring local flow within a boundary layer away from an outer solid wall of a vehicle comprising:

needle means having a square end forming a block and having flat sides and a pyramid-shaped tip having four faces for measuring orthogonal shear stress within a boundary layer;

a probe having a tapered leading end attached to said means for measuring with a trailing end having outlets for electrical leads;

electrical leads connected to said means for measuring and leading through said probe; and means for generating end displaying shear stress management attacked to said electrical leads.

7. An orthogonal shear stress measuring probe assembly as in claim 6 wherein said means for measuring orthogonal shear stresses further comprises a plurality of micron-sized floating element drag sensors, said sensors being affixed to each side of the block formed by the modified needle and to each face of the pyramid-shaped tip.

8. An orthogonal shear stress measuring probe assembly for measuring local flow within a boundary layer away from an outer solid wall of a vehicle comprising:

a needle with micron-sized floating elements attached thereto, said needle having a hexagon-shaped end section forming a six-sided block and further having a pyramid-shaped tip having four faces forming a pyramid, each of six sides of said block and each of said four faces of said pyramid having tethers including piezoelectric elements for generating a plurality of electrical signals in response to stresses on said six sides of said block and said four faces of said pyramid;

said probe assembly having a tapered leading end, attached to said needle, with a trailing end having outlets for electrical leads for transmitting said plurality of electrical signals;

said electrical leads connected to means for measuring said plurality of electrical signals and leading through said probe assembly; and means for generating and displaying said plurality of electrical signals and correlating them to said shear stressor on said six sides of said block and said four faces of said pyramid.

* * * * *